US009929006B2

United States Patent
Quick et al.

(10) Patent No.: US 9,929,006 B2
(45) Date of Patent: Mar. 27, 2018

(54) SILICON CHALCOGENATE PRECURSORS, METHODS OF FORMING THE SILICON CHALCOGENATE PRECURSORS, AND RELATED METHODS OF FORMING SILICON NITRIDE AND SEMICONDUCTOR STRUCTURES

(71) Applicant: Micron Technology, Inc., Boise, ID (US)

(72) Inventors: Timothy A. Quick, Boise, ID (US); Sumeet C. Pandey, Boise, ID (US); Stefan Uhlenbrock, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 0 days.

(21) Appl. No.: 15/215,102

(22) Filed: Jul. 20, 2016

(65) Prior Publication Data

US 2018/0025906 A1    Jan. 25, 2018

(51) Int. Cl.
*H01L 21/31* (2006.01)
*H01L 21/02* (2006.01)
(Continued)

(52) U.S. Cl.
CPC ...... *H01L 21/02208* (2013.01); *C01B 21/068* (2013.01); *C07F 7/025* (2013.01);
(Continued)

(58) Field of Classification Search
CPC ......... H01L 21/02219; H01L 21/02208; H01L 21/02222; H01L 21/76831; H01L 21/0228;
(Continued)

(56) References Cited

U.S. PATENT DOCUMENTS 8,647,993 B2    2/2014  LaVoie et al.
9,385,318 B1 *  7/2016  Henri .................. H01L 45/1616
(Continued)

FOREIGN PATENT DOCUMENTS

WO    2016065221 A1    4/2016

OTHER PUBLICATIONS

Anderson et al., Methylseleno—Derivatives of Group IV, J. Chem. Soc., Dalton Trans., (1973), pp. 1716-1724.
International Search Report from International Application No. PCT/US2017/040662, dated Oct. 13, 2017, 3 pages.
International Written Opinion from International Application No. PCT/US2017/040662, dated Oct. 13, 2017, 4 pages.

*Primary Examiner* — Thanh T Nguyen
(74) *Attorney, Agent, or Firm* — TraskBritt

(57) ABSTRACT

A silicon chalcogenate precursor comprising the chemical formula of $Si(XR^1)_n R^2_{4-n}$, where X is sulfur, selenium, or tellurium, $R^1$ is hydrogen, an alkyl group, a substituted alkyl group, an alkoxide group, a substituted alkoxide group, an amide group, a substituted amide group, an amine group, a substituted amine group, or a halogen group, each $R^2$ is independently hydrogen, an alkyl group, a substituted alkyl group, an alkoxide group, a substituted alkoxide group, an amide group, a substituted amide group, an amine group, a substituted amine group, or a halogen group, and n is 1, 2, 3, or 4. Methods of forming the silicon chalcogenate precursor, methods of forming silicon nitride, and methods of forming a semiconductor structure are also disclosed.

18 Claims, 2 Drawing Sheets

(51) Int. Cl.
   *C01B 21/068*   (2006.01)
   *C09D 7/12*    (2006.01)
   *C07F 7/02*    (2006.01)
   *H01L 21/768*   (2006.01)

(52) U.S. Cl.
   CPC ........ *C09D 7/1233* (2013.01); *H01L 21/0217* (2013.01); *H01L 21/0228* (2013.01); *H01L 21/76831* (2013.01)

(58) Field of Classification Search
   CPC ........... H01L 21/0217; H01L 21/02642; H01L 21/02126; H01L 21/214; H01L 29/78684; H01L 29/7869
   See application file for complete search history.

(56) References Cited

U.S. PATENT DOCUMENTS

| | | | |
|---|---|---|---|
| 9,601,693 B1* | 3/2017 | Henri | H01L 45/16 |
| 2009/0163023 A1* | 6/2009 | Song | H01L 45/06 |
| | | | 438/652 |
| 2011/0256718 A1 | 10/2011 | Haukka et al. | |
| 2013/0071580 A1 | 3/2013 | Weidman et al. | |
| 2014/0141542 A1 | 5/2014 | Kang et al. | |
| 2014/0273528 A1 | 9/2014 | Niskanen et al. | |
| 2015/0099375 A1 | 4/2015 | Haripin et al. | |
| 2015/0259791 A1 | 9/2015 | Hausmann et al. | |
| 2016/0079054 A1 | 3/2016 | Chen et al. | |
| 2016/0093484 A1 | 3/2016 | Marsh | |
| 2016/0108518 A1 | 4/2016 | Park et al. | |
| 2016/0148806 A1 | 5/2016 | Henri et al. | |

* cited by examiner

SILICON CHALCOGENATE PRECURSORS, METHODS OF FORMING THE SILICON CHALCOGENATE PRECURSORS, AND RELATED METHODS OF FORMING SILICON NITRIDE AND SEMICONDUCTOR STRUCTURES

TECHNICAL FIELD

Embodiments disclosed herein relate to semiconductor fabrication including precursor compounds for forming silicon nitride, methods of forming the precursor compounds, methods of forming the silicon nitride, and methods of forming semiconductor structures. More particularly, embodiments of the disclosure relate to silicon chalcogenate precursors, methods of forming the silicon chalcogenate precursors, methods of forming the silicon nitride using the silicon chalcogenate precursors, and methods of forming semiconductor structures.

BACKGROUND

Silicon nitride (SiN) is a widely used material in the manufacturing of integrated circuits (ICs). Due to its low reactivity and high thermal stability, silicon nitride is used as an insulating material, a mask material, an etch-stop material, a barrier material, a spacer material, etc.

Techniques for forming SiN include physical vapor deposition (PVD) and chemical vapor deposition (CVD), such as high temperature thermal CVD or plasma-enhanced CVD (PECVD). In one process, silane ($SiH_4$) is reacted with ammonia ($NH_3$) to form the SiN. Other silicon precursors may be used, such as silicon halides including silicon fluorides, silicon chlorides, silicon iodides, or silicon bromides. Examples of silicon halides include, but are not limited to, silicon tetrachloride ($SiCl_4$) or dichlorosilane ($SiCl_2H_2$), trichlorosilane ($SiHCl_3$), $HSiI_3$, $H_2SiI_2$, $H_3SiI$, $H_2Si_2I_4$, $H_4Si_2I_2$, or $H_5Si_2I$. To form high quality SiN, the PVD and CVD processes are conducted at high temperatures, usually greater than 750° C. However, these temperatures are not compatible with materials used in current ICs, some of which are thermally sensitive. Additionally, using a silicon halide as the silicon precursor is not desirable because reactive halide species, such as hydrochloric acid (HCl), are produced as byproducts. The reactive halide species are known to etch materials used in semiconductor fabrication, such as silicon-containing materials.

Atomic layer deposition (ALD) has also been used to form SiN. The silane, silicon halide, and ammonia CVD precursors are sufficiently reactive at high temperatures or in a plasma environment to form SiN by ALD. However, the precursors are not sufficiently reactive at low temperatures or without a plasma. While plasma-enhanced ALD (PEALD) has been used to form SiN and increased conformality and decreased deposition temperatures have been achieved compared to the conformality and deposition temperatures of CVD processes, step coverage of the SiN is not sufficiently conformal to cover complex topographies present in current ICs. In addition, excited species created during the plasma portion of the PEALD process are not selective to exposed materials on the ICs and, therefore, unintended reactions between the excited species and the exposed materials occur. Even in the absence of a plasma, the silicon precursor needs to be carefully selected to avoid these unintended reactions, which can result in degradation of IC performance.

Silylamine-based compounds, such as bis[(dimethylamino)methylsilyl](tri-methylsilyl)amine, bis[(diethylamino)dimethylsilyl](trimethylsilyl)amine, or tris[(diethylamino)-dimethylsilyl]amine, have also been proposed as silicon precursors for ALD processes.

As deposition requirements for SiN become more stringent, the techniques mentioned above have not been able to form SiN at the desired degree of conformality and at low temperatures.

DETAILED DESCRIPTION

Figure 1:
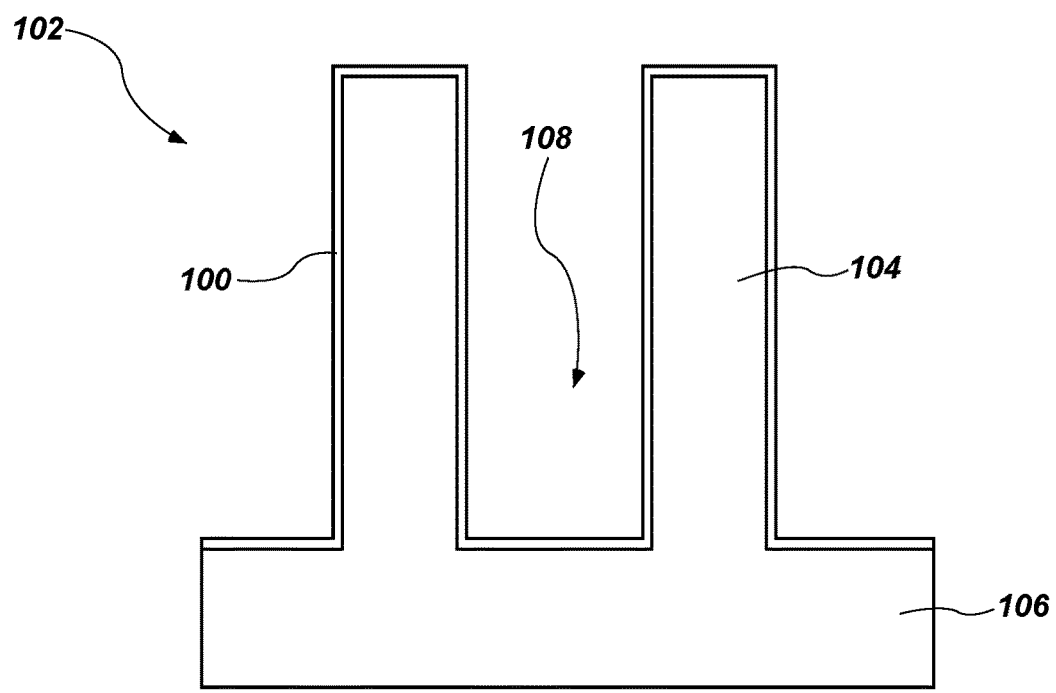
FIG. 1 is a simplified cross-sectional view of a semiconductor structure including a silicon nitride material formed in accordance with embodiments of the disclosure.

Silicon chalcogenate precursors are disclosed, as are methods of forming the silicon chalcogenate precursors and methods of forming silicon nitride (SiN) using the silicon chalcogenate precursors. The SiN may be formed on a substrate by an ALD process at a low temperature and without using a plasma. The silicon chalcogenate precursor may be sufficiently reactive with a reducing agent to form the SiN while still exhibiting stability under reaction conditions of the ALD process. The SiN formed by the methods of the disclosure may have a high degree of conformality, such as greater than about 90% step coverage, enabling the SiN to be formed on high density, high aspect ratio semiconductor structures. Since the SiN is formed at a low temperature, the methods of the disclosure are compatible with thermally sensitive materials that may be exposed during the ALD process. In addition, while the silicon chalcogenate precursors may include halogen atoms, the methods of the disclosure do not produce reactive halogen-containing species (i.e., are free of the reactive halogen-containing species) and do not use a plasma (i.e., are plasma free). The silicon chalcogenate precursors are, thus, suitable replacements for silicon halide precursors.

As used herein, the term "silicon chalcogenate" means and includes a compound including at least one silicon atom and at least one chalcogen atom, and includes at least one silicon-chalcogen bond. The silicon chalcogenate is analogous to a silicon alkoxide except with a sulfur atom, a selenium atom, or a tellurium atom replacing the oxygen atom of the silicon alkoxide. The chalcogen includes an element of Group VI of the Periodic Table, such as sulfur, selenium, or tellurium.

As used herein, the term "silicon nitride" means and includes a compound including silicon atoms and nitrogen atoms. The silicon nitride may include stoichiometric amounts of silicon and nitrogen, such as $Si_3N_4$, or may include non-stoichiometric amounts of silicon and nitrogen, such as $Si_xN_y$, where each of x and y is independently a rational number from about 0.5 to about 2.0. The silicon nitride may also include $Si(CH)_xN_y$, where each of x and y is independently a rational number from about 0 to about 2.0.

As used herein, the term "substrate" means and includes a base material or construction upon which additional materials are formed. The substrate may be a semiconductor substrate, a base semiconductor layer on a supporting structure, a metal electrode, or a semiconductor substrate having one or more materials, layers, structures, or regions formed thereon. The materials on the semiconductor structure may include, but are not limited to, semiconductive materials, insulating materials, conductive materials, etc. One or more of the materials may be thermally sensitive. The substrate may be a conventional silicon substrate or other bulk substrate comprising a layer of semiconductive material. As used herein, the term "bulk substrate" means and includes not only silicon wafers, but also silicon-on-insulator ("SOI") substrates, such as silicon-on-sapphire ("SOS") substrates and silicon-on-glass ("SOG") substrates, epitaxial layers of silicon on a base semiconductor foundation, and other semiconductor or optoelectronic materials, such as silicon-germanium, germanium, gallium arsenide, gallium nitride, and indium phosphide. The substrate may be doped or undoped.

As used herein, the term "aspect ratio" means and includes a ratio of a height of a feature to a width of the feature.

The following description provides specific details, such as material types, material thicknesses, and processing conditions in order to provide a thorough description of embodiments described herein. However, a person of ordinary skill in the art will understand that the embodiments disclosed herein may be practiced without employing these specific details. Indeed, the embodiments may be practiced in conjunction with conventional fabrication techniques employed in the semiconductor industry. In addition, the description provided herein does not form a complete description of a semiconductor structure or a complete process flow for manufacturing semiconductor structures and the structures described below do not form a complete semiconductor structure. Only those process acts and structures necessary to understand the embodiments described herein are described in detail below. Additional acts to form a complete semiconductor structure including the structures described herein may be performed by conventional techniques.

The silicon chalcogenate precursor may have the chemical formula of $Si(XR^1)_n R^2_{4-n}$ where X is sulfur, selenium, or tellurium, $R^1$ is hydrogen, an alkyl group, a substituted alkyl group, an alkoxide group, a substituted alkoxide group, an amide group, a substituted amide group, an amine group, a substituted amine group, or a halogen group, each $R^2$ is independently hydrogen, an alkyl group, a substituted alkyl group, an alkoxide group, a substituted alkoxide group, an amide group, a substituted amide group, or a halide group, and n is 1, 2, 3, or 4. Each of X, $R^1$, and $R^2$ is independently selected to provide the desired reactivity of the silicon chalcogenate precursor with the reducing agent and to provide the desired stability to the silicon chalcogenate precursor. Each $R^2$ may independently include a halogen atom directly or indirectly bonded to the silicon atom while the remaining substituent (i.e., $R^1$) includes a halogen atom (if one is present) only indirectly bonded to the silicon atom. Thus, multiple halogen atoms may be present in the silicon chalcogenate precursor.

As used herein, the term "alkyl" means and includes a saturated, unsaturated, straight, branched, or cyclic hydrocarbon chain including from one carbon atom ($C_1$) to ten carbon atoms ($C_{10}$), such as from one carbon atom ($C_1$) to six carbon atoms ($C_6$).

As used herein, the term "alkoxide" means and includes an alkyl group linked to an oxygen atom including, but not limited to, a methoxy group, an ethoxy group, a propoxy group, a butoxy group, a pentoxy group, a hexoxy group, a heptoxy group, an octoxy group, a nonoxy group, or a decoxy group, or an alkoxy-substituted alkoxy group (e.g., a polyether group), such as a methoxy methoxy group, a methoxy ethoxy group, an ethoxy methoxy group, an ethoxy ethoxy group, a methoxy ethoxy ethoxy group, etc.

As used herein, the term "substituted" means and includes a functional group where one or more hydrogen atoms have been replaced by another functional group, such as an alkyl group, an alkoxide group, an amide group, an amine group, or a halogen group.

As used herein, the term "amide" means and includes a —NR'R" group where R' and R" are independently an alkyl group, a substituted alkyl group, an alkoxide group, a substituted alkoxide group, an amide group, a substituted amide group, an amine group, a substituted amine group, or a halogen group.

As used herein, the term "amine" means and includes an —NH$_2$ group.

As used herein, the term "halogen" means and includes fluoro, chloro, bromo, or iodo.

The silicon chalcogenate precursor may have the chemical formula of:

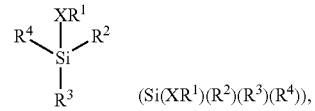
$(Si(XR^1)(R^2)(R^3)(R^4))$, where X, $R^1$, and $R^2$ are as defined above and each of $R^3$ and $R^4$ is independently hydrogen, an alkyl group, a substituted alkyl group, an alkoxide group, a substituted alkoxide group, an amide group, a substituted amide group, or a halide group. The silicon chalcogenate precursor may alternatively include two, three, or four —X— groups directly bonded to the silicon atom, such as $Si(XR^1)(XR^2)(R^3)(R^4)$, $Si(XR^1)(R^2)(XR^3)(R^4)$, $Si(XR^1)(XR^2)(R^3)(XR^4)$, $Si(XR^1)(XR^2)(XR^3)(R^4)$, $Si(XR^1)(R^2)(XR^3)(XR^4)$, or $Si(XR^1)(XR^2)(XR^3)(XR^4)$. In one embodiment, the silicon chalcogenate is silicon tetramethylselenoate $(Si(Se(CH_3)_4))$.

The X, $R^1$, and $R^2$ groups and value for n may be selected based on the intended application for the SiN. For instance, if a highly reactive and stable silicon chalcogenate precursor is desired, the silicon chalcogenate precursor may include four chalcogen atoms, e.g., a compound having the chemical formula of $Si(XR^1)(XR^2)(XR^3)(XR^4)$. However, if a less reactive and stable silicon chalcogenate precursor is needed, the silicon chalcogenate precursor may include fewer chalcogen atoms, i.e., a compound having the chemical formula of $Si(XR^1)(R^2)(R^3)(R^4)$, $Si(XR^1)(XR^2)(R^3)(R^4)$, $Si(XR^1)(R^2)(XR^3)(R^4)$, $Si(XR^1)(XR^2)(R^3)(XR^4)$, $Si(XR^1)(XR^2)(XR^3)(R^4)$, or $Si(XR^1)(R^2)(XR^3)(XR^4)$.

If halogen atoms are present to provide the desired balance between reactivity with the reducing agent and stability, each of $R^2$, $R^3$, and $R^4$ may include a halogen atom directly or indirectly bonded to the silicon atom. For example, it is contemplated that each of $R^2$, $R^3$, and $R^4$ may include a halogen atom directly or indirectly bonded to the silicon atom. If a halogen atom is present on $R^1$, the halogen atom is indirectly bonded to the silicon atom through the chalcogen atom X. In the situation where only $R^1$ includes a halogen atom, the halogen atom is indirectly bonded to the silicon atom of the silicon chalcogenate precursor through the chalcogen atom X. There is, thus, no direct silicon-halogen bond at the $R^1$ position because the chalcogen atom is directly bonded to the silicon atom, with the halogen atom directly bonded to the chalcogen atom. In the situation where one or more of $R^2$, $R^3$, or $R^4$ includes a halogen atom, the halogen atom may be directly or indirectly bonded to the silicon atom. To provide the desired balance of reactivity and stability to the silicon chalcogenate precursor, one or more of $R^2$, $R^3$, or $R^4$ independently includes the halogen atom directly or indirectly bonded to the silicon atom while the remaining substituent (i.e., $R^1$) only includes a halogen atom (if one is present) indirectly bonded to the silicon atom.

Accordingly, a silicon chalcogenate precursor is disclosed and comprises the chemical formula of $Si(XR^1)_nR^2_{4-n}$, where X is sulfur, selenium, or tellurium, $R^1$ is hydrogen, an alkyl group, a substituted alkyl group, an alkoxide group, a substituted alkoxide group, an amide group, a substituted amide group, an amine group, a substituted amine group, or a halogen group, each $R^2$ is independently hydrogen, an alkyl group, a substituted alkyl group, an alkoxide group, a substituted alkoxide group, an amide group, a substituted amide group, an amine group, a substituted amine group, or a halogen group, and n is 1, 2, 3, or 4.

The silicon chalcogenate precursor according to embodiments of the disclosure is sufficiently reactive with the reducing agent, such as a nitrogen-containing precursor, to form the SiN by the ALD process. However, the silicon chalcogenate precursor is also sufficiently stable to be used under vapor delivery conditions of the ALD process. The silicon chalcogenate precursor exhibits a similar reactivity with the reducing agent as a conventional silicon halide precursor. The nitrogen-containing precursor may include, but is not limited to, ammonia ($NH_3$), hydrazine ($N_2H_4$), t-butyl hydrazine, a monoalkylhydrazine, a dialkylhydrazine, or combinations thereof. In one embodiment, the nitrogen-containing precursor is ammonia. The silicon chalcogen precursor is used as the source of silicon for the SiN and the nitrogen-containing precursor is used as the source of nitrogen for the SiN.

Although the silicon chalcogenate precursor according to embodiments of the disclosure may include multiple halogen atoms, the silicon chalcogenate precursor may nonetheless be compatible with sensitive materials that are present on the substrate and exposed during the ALD process because no reactive halogen-containing species are produced as byproducts. Thus, no halide byproduct contamination is observed during the ALD process.

The silicon chalcogenate precursor may be formed by reacting an organolithium reagent or Grignard reagent with a chalcogen source compound to produce an organolithium chalcogen compound. The organolithium reagent may be appropriately selected depending on the desired $R^1$ and $R^2$ groups of the silicon chalcogenate precursor. The organolithium may include an alkyllithium reagent, such as methyllithium, ethyllithium, etc. The chalcogen source compound may be appropriately selected depending on the desired chalcogen of the silicon chalcogenate precursor. The chalcogen source compound may be elemental sulfur, elemental selenium, elemental tellurium, or combinations thereof. The organolithium chalcogen compound may then be reacted with a silicon halide compound to form the silicon chalcogenate precursor. The silicon halide may include, but is not limited to, a compound of silicon and fluorine, a compound of silicon and chlorine, a compound of silicon and bromine, or a compound of silicon and iodine. The organolithium chalcogen compound and silicon halide may be reacted at a low temperature, such as below room temperature or below 0° C., to produce the silicon chalcogenate precursor.

Accordingly, a method of forming a silicon chalcogenate precursor is disclosed. The method comprises reacting an organolithium reagent with a chalcogen source compound to produce an organolithium chalcogen compound. The organolithium chalcogen compound is reacted with a silicon halide compound to form the silicon chalcogenate precursor. The silicon chalcogenate precursor comprises the chemical formula of $Si(XR^1)_nR^2_{4-n}$, where X is sulfur, selenium, or tellurium, $R^1$ is hydrogen, an alkyl group, a substituted alkyl group, an alkoxide group, a substituted alkoxide group, an amide group, a substituted amide group, an amine group, a substituted amine group, or a halogen group, each $R^2$ is independently hydrogen, an alkyl group, a substituted alkyl group, an alkoxide group, a substituted alkoxide group, an amide group, a substituted amide group, an amine group, a substituted amine group, or a halogen group, and n is 1, 2, 3, or 4.

To form the SiN by ALD, the silicon chalcogenate precursor and nitrogen-containing precursor may be sequentially introduced into a reactor containing the substrate and the precursors reacted with a surface of the substrate. The silicon chalcogenate precursor may be introduced into the reactor, reacted with the substrate, and excess unreacted silicon chalcogenate precursor purged from the reactor to form silicon on the substrate. A monolayer or less of the silicon may be formed. The nitrogen-containing precursor may then be introduced into the reactor, reacted with the silicon on the substrate, and excess unreacted nitrogen-containing precursor purged from the reactor to form nitrogen on the silicon. A monolayer or less of the nitrogen may be formed. The reactor may be a conventional reaction chamber or a conventional deposition chamber, such as a conventional ALD reactor or a conventional CVD reactor, which are not described in detail here. During the ALD process, silicon from the silicon chalcogenate precursor and nitrogen from the nitrogen-containing precursor are adsorbed to the surface of the substrate. The order of introducing the silicon chalcogenate precursor and nitrogen-containing precursor may be reversed such that the nitrogen-containing precursor is introduced into the reactor, reacted with the surface of the substrate, and excess unreacted nitrogen-containing precursor purged from the reactor to form nitrogen on the substrate. Then, the silicon chalcogenate precursor may be introduced into the reactor, reacted with the nitrogen, and excess unreacted silicon chalcogenate precursor purged from the reactor to form silicon on the nitrogen. The introduction of the silicon chalcogenate precursor and nitrogen-containing precursor may, optionally, include a carrier gas, such as helium, argon, nitrogen, or combinations thereof. The process of sequentially introducing the silicon chalcogenate precursor and nitrogen-containing precursor may be repeated for a desired number of cycles until a desired thickness of the SiN is obtained. In between each introduction of the silicon chalcogenate precursor and nitrogen-containing precursor, the reactor may, optionally, be purged with a purge gas to remove the unreacted silicon chalcogenate precursor and nitrogen-containing precursor or reaction byproducts. The purge gas may be an inert gas, such as helium, argon, nitrogen, or combinations thereof.

In an embodiment where the nitrogen-containing precursor is ammonia, the ALD process may proceed according to the following reaction:

$$Si(XR^1_n)R^2_{4-n}+NH_3 \rightarrow Si_xN_y+HXR^1+HR^2.$$

The ALD process may be conducted at a temperature of less than or equal to about 350° C., such as less than or equal to about 250° C. The temperature within the reactor and of the substrate may be at or less than about 350° C. while the ALD process occurs. The low temperature at which the SiN is formed may reduce the thermal budget relative to that of conventional high temperature thermal CVD, PECVD, or PVD processes of forming SiN. The low temperature may also enable the SiN to be conformally formed although sensitive materials are present on the substrate. Without limitation, the sensitive materials may include, but are not limited to, chalcogenide materials, organic (e.g., carbon) materials, carbon allotropes (e.g., graphite), reactive metals (e.g., tungsten, aluminum, or tantalum) or other sensitive materials. Thus, the SiN may be formed adjacent to such sensitive materials without degrading, decomposing, or otherwise negatively affecting the materials.

Each of the silicon chalcogenate precursor, nitrogen-containing precursor, and purge gas may be introduced into the reactor at a flow rate of from about 1 standard cubic centimeters (sccm) to about 2000 sccm, such as from about 1 sccm to about 1000 sccm. Each of the silicon chalcogenate precursor and nitrogen-containing precursor may remain in the reactor for an amount of time ranging from about 0.1 second to 100 seconds, sufficient for the silicon chalcogenate precursor and nitrogen-containing precursor to react.

The silicon chalcogenate precursor and nitrogen-containing precursor may be sufficiently reactive that a plasma is not needed. Thus, the ALD process may be conducted without generating a plasma. However, depending on the thermal sensitivity of adjacent and exposed materials on the substrate, a plasma may be used to increase the reactivity of the silicon chalcogenate precursor and nitrogen-containing precursor. For instance, if the adjacent and exposed materials on the substrate are not thermally sensitive or are less thermally sensitive, the deposition temperature may be increased or a plasma may be used. The plasma may be generated in the reactor (e.g., a direct plasma) or the plasma may be generated outside the reactor and supplied to the reactor (e.g., a remote plasma).

Without being bound by any theory, it is believed that the silicon chalcogenate precursor according to embodiments of the disclosure is stable yet exhibits a similar reactivity with the nitrogen-containing precursor as a conventional silicon halide precursor. Therefore, the silicon chalcogenate precursors according to embodiments of the disclosure are thermally stable and do not readily decompose. By way of example only, if the silicon chalcogenate precursor is silicon tetramethylselenoate ($Si(SeCH_3)_4$), the silicon chalcogenate precursor may decompose according to one of the following pathways:

| Decomposition Pathway | $E_a$ (kJ/mol) | dE (kJ/mol) |
|---|---|---|
| $Si(SeCH_3)_4 \rightarrow SiH(SeCH_3)_3 + SeCH_2$ | 347.1 | 183.9 |
| $Si(SeCH_3)_4 \rightarrow SiSe(SeCH_3)_2 + Se(CH_3)_2$ | 246.1 | 56.7 |
| $Si(SeCH_3)_4 \rightarrow Si(SeCH_3)_2 + CH_3SeSeCH_3$ | 300.9 | 214.5 |
| $Si(SeCH_3)_4 \rightarrow Si(CH_3)_2(SeCH_3)_2 + Se_2$ | 293.0 | 118.5 |

It is believed that the high activation energies ($E_a$) (i.e., energy barriers) and endothermic nature of the decomposition pathways provide the desired properties to the silicon chalcogenate precursor.

Accordingly, a method of forming SiN is disclosed. The method comprises reacting a silicon chalcogenate precursor and a nitrogen-containing precursor to form silicon nitride. The silicon chalcogenate precursor comprises the chemical formula of $Si(XR^1)_n R^2_{4-n}$, where X is sulfur, selenium, or tellurium, $R^1$ is hydrogen, an alkyl group, a substituted alkyl group, an alkoxide group, a substituted alkoxide group, an amide group, a substituted amide group, an amine group, a substituted amine group, or a halogen group, each $R^2$ is independently hydrogen, an alkyl group, a substituted alkyl group, an alkoxide group, a substituted alkoxide group, an amide group, a substituted amide group, an amine group, a substituted amine group, or a halogen group, and n is 1, 2, 3, or 4.

Accordingly, another method of forming SiN is disclosed. The method comprises reacting a silicon chalcogenate precursor with a substrate to form silicon on the substrate, reacting the silicon with a nitrogen-containing precursor to form nitrogen on the silicon, and repeating the reacting a silicon chalcogenate precursor and reacting the silicon with a nitrogen-containing precursor acts. The silicon chalcogenate precursor comprises the chemical formula of $Si(XR^1)_n R^2_{4-n}$, where X is sulfur, selenium, or tellurium, $R^1$ is hydrogen, an alkyl group, a substituted alkyl group, an alkoxide group, a substituted alkoxide group, an amide group, a substituted amide group, an amine group, a substituted amine group, or a halogen group, each $R^2$ is independently hydrogen, an alkyl group, a substituted alkyl group, an alkoxide group, a substituted alkoxide group, an amide group, a substituted amide group, an amine group, a substituted amine group, or a halogen group, and n is 1, 2, 3, or 4.

By way of example only, the SiN may be formed to a thickness ranging from a few monolayers to about 100 nm, such as from about 1 nm to about 100 nm or from about 5 nm to about 50 nm. However, the SiN may also be formed at greater thicknesses.

The illustrations included herewith are not meant to be actual views of any particular semiconductor structure, but are merely idealized representations that are employed to describe embodiments herein. Thus, the illustrations may not be drawn to scale.

As shown in FIG. 1, SiN 100 may be conformally formed on a semiconductor structure 102 having at least one feature 104 with a high aspect ratio. The semiconductor structure 102 may include a substrate 106 having openings 108 therein that define the features 104. Depending on the intended application for the SiN 100, the substrate 106 may be a semiconductive material, an insulating material, or a conductive material. By way of example only, the semiconductive material may be silicon, a silicon oxide, gallium, etc. By way of example only, the insulating material may be silicon dioxide, hafnium oxide, aluminum oxide. By way of example only, the conductive material may be a metal, a conductively-doped silicon, a conductively-doped germanium, a metal silicide, a metal carbide, a phase change material, etc. The material of the substrate 106 may be formed by conventional techniques, such as physical vapor deposition (PVD), chemical vapor deposition (CVD), or atomic layer deposition (ALD). Such techniques are known in the art and, therefore, are not described in detail herein. As shown in FIG. 1, the features 104 are formed from the material of the substrate 106. However, the substrate 106 may include one or more materials, layers, structures, or regions thereon, such as a stack structure, which makes up the features 104. The materials of the stack structure may be formed by conventional techniques, which are not described in detail herein. The features 104 may have a high aspect ratio, such as an aspect ratio of at least 10:1, such as at least 12:1 or at least 15:1. The SiN 100 may be formed over the features 104 according to embodiments of the disclosure. The SiN 100 may, alternatively, be formed on the semiconductor structure 102 as a planar layer (not shown). The SiN may be used in any semiconductor device structure, such as in a transistor, memory, logic device, memory array, etc., as an insulating material, a mask material, an etch-stop material, a barrier material, or a spacer material. The semiconductor device structure may include at least one high aspect ratio feature.

Accordingly, a method of forming a semiconductor structure is disclosed. The method comprises forming a substrate comprising at least one feature having an aspect ratio of greater than about 10 and reacting a silicon chalcogenate precursor and a nitrogen-containing precursor to form silicon nitride on the at least one feature.

While methods of forming the SiN by an ALD process are described above, the silicon chalcogenate precursor may also be used as a silicon precursor in a CVD process. The CVD process may be substantially as described above except that the silicon chalcogenate precursor and nitrogen-containing precursor are simultaneously introduced into a CVD reactor and appropriate operating conditions selected for the CVD process.

The following examples serve to explain embodiments of the disclosure in more detail. These examples are not to be construed as being exhaustive or exclusive as to the scope of this disclosure.

EXAMPLES

Synthesis of Silicon Tetramethylselenoate

As shown in the reaction schemes below, a slight excess of methyllithium (MeLi) was reacted with selenium (Se) in tetrahydrofuran or diglyme to form lithium methylselenide (LiSeMe). Four equivalents of LiSeMe are reacted with silicon tetrachloride at −76° C. to form the silicon tetramethylselenoate, which is recovered.

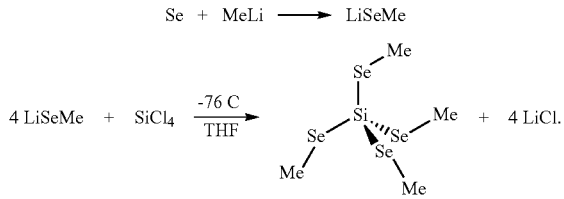

Activation Energy and Change in Energy Calculations

Density functional theory (DFT) calculations were conducted for the reaction of $Si(SeCH_3)_4$ with $NH_3$. For comparison, similar calculations were conducted for the reaction of $SiCl_4$ with $NH_3$. The calculated activation energies ($E_a$) and change in energy (dE) are shown below:

| Reaction | $E_a$ (kJ/mol) | dE (kJ/mol) |
|---|---|---|
| $Si(SeCH_3)_4 + NH_3$ | 132.1 | −16.9 |
| $SiCl_4 + NH_3$ | 116 | −9.2 |

Both reactions were determined to be exothermic and exhibit similar energy barriers (132.1 kJ/mol and 116 kJ/mol, respectively).

The comparable reactivity to ammonia of the silicon tetramethylselenoate and the silicon tetrachloride was surprising because analogous precursors where an oxygen atom replaces the chalcogen atom are not similarly reactive.

Effect on $E_a$/dE by Different Silicon-Ligand Systems

Figure 2:
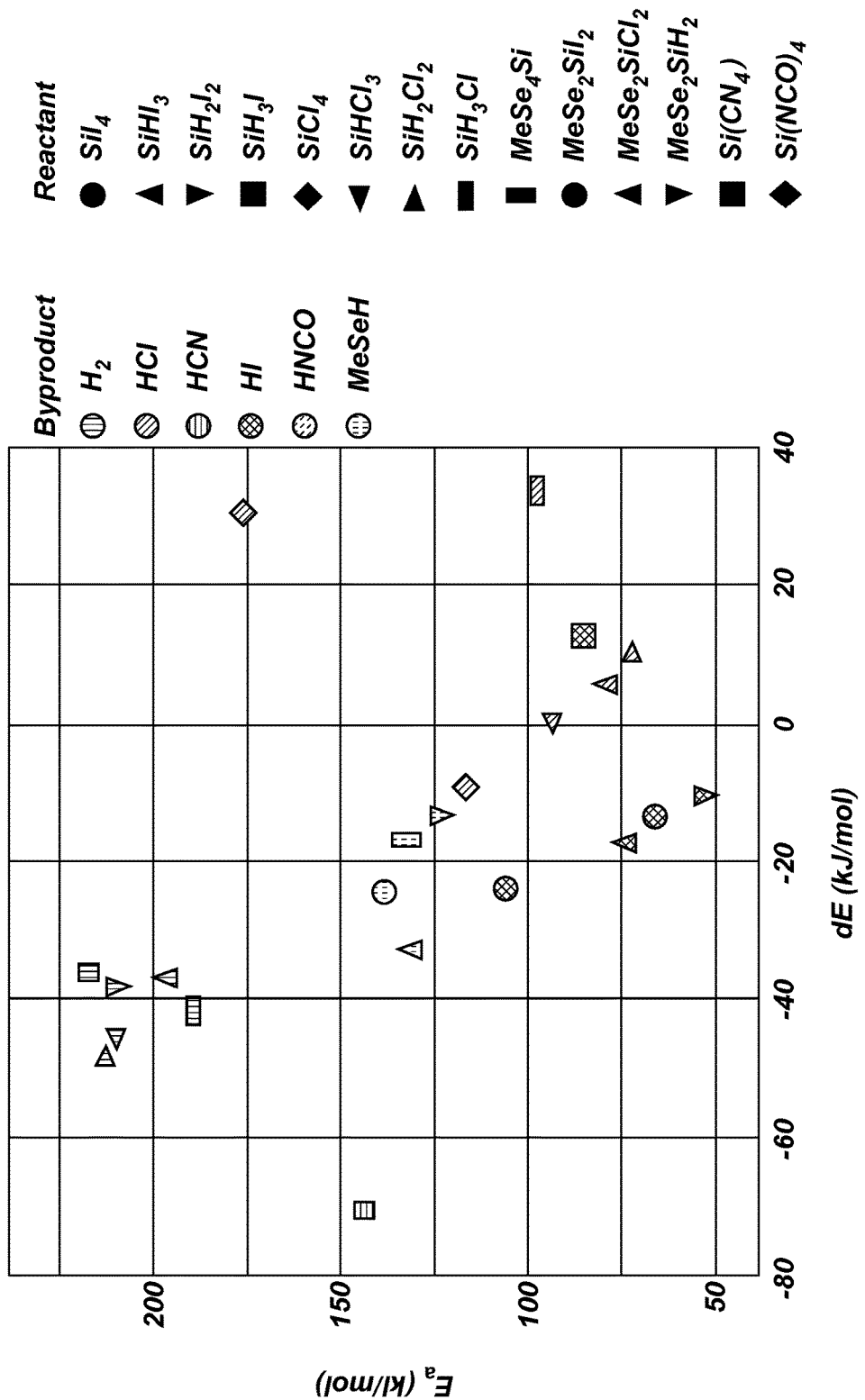
FIG. 2 is a plot of activation energy ($E_a$) as a function of change in energy (dE) for silicon-ligand (Si—R) systems reacted with ammonia.

The activation energies ($E_a$) (i.e., energy barriers) and changes in energy (dE) for the reaction of different silicon-ligand (Si—R) systems with ammonia were calculated to determine the effect of the ligand (R) on bond strength. The ligands included H, I, Cl, CN, NCO, or $SeCH_3$. FIG. 2 shows the activation energy ($E_a$) plotted as a function of change in energy (dE) for each Si—R system. Depending on the Si—R system used, $H_2$, HCl, HCN, HI, HNCO, or MeSeH were produced as byproducts. The silicon chalcogenate precursor, which exhibited MeSeH elimination, had lower activation energies than the Si—R systems that exhibited $H_2$ elimination. While other Si—R systems exhibited lower activation energies than those including selenium, the dE of these Si—R systems were not as favorable as the Si—R systems including selenium. The Si—R systems including selenium had slightly higher activation energies than the silicon-chlorine system. However, since halide byproducts are not produced by the silicon-$SeCH_3$ systems, no problems associated with undesirable etching of materials are observed.

While certain illustrative embodiments have been described in connection with the figures, those of ordinary skill in the art will recognize and appreciate that embodiments encompassed by the disclosure are not limited to those embodiments explicitly shown and described herein. Rather, many additions, deletions, and modifications to the embodiments described herein may be made without departing from the scope of embodiments encompassed by the disclosure, such as those hereinafter claimed, including legal equivalents. In addition, features from one disclosed embodiment may be combined with features of another disclosed embodiment while still being encompassed within the scope of the disclosure.

What is claimed is:
1. A method of forming silicon nitride, comprising:
reacting a silicon chalcogenate precursor and a nitrogen-containing precursor to form silicon nitride, the silicon chalcogenate precursor comprising the chemical formula of $Si(XR^1)_nR^2_{4-n}$, where X is sulfur, selenium, or tellurium, $R^1$ is hydrogen, an alkyl group, a substituted alkyl group, an alkoxide group, a substituted alkoxide group, an amide group, a substituted amide group, an amine group, a substituted amine group, or a halogen group, each $R^2$ is independently hydrogen, an alkyl group, a substituted alkyl group, an alkoxide group, a substituted alkoxide group, an amide group, a substituted amide group, an amine group, a substituted amine group, or a halogen group, and n is 1, 2, 3, or 4.

2. The method of claim 1, wherein reacting a silicon chalcogenate precursor and a nitrogen-containing precursor to form silicon nitride comprises forming the silicon nitride by atomic layer deposition.

3. The method of claim 1, wherein reacting a silicon chalcogenate precursor and a nitrogen-containing precursor to form silicon nitride comprises forming the silicon nitride by chemical vapor deposition.

4. The method of claim 1, wherein reacting a silicon chalcogenate precursor and a nitrogen-containing precursor to form silicon nitride comprises conformally forming the silicon nitride on a substrate.

5. The method of claim 1, wherein reacting a silicon chalcogenate precursor and a nitrogen-containing precursor to form silicon nitride comprises reacting the silicon chalcogenate precursor with ammonia, hydrazine, t-butyl hydrazine, a monoalkylhydrazine, a dialkylhydrazine, or combinations thereof.

6. The method of claim 1, wherein reacting a silicon chalcogenate precursor and a nitrogen-containing precursor to form silicon nitride comprises forming the silicon nitride at a temperature of less than or equal to about 350° C.

7. The method of claim 1, wherein reacting a silicon chalcogenate precursor and a nitrogen-containing precursor to form silicon nitride comprises forming the silicon nitride at a temperature of less than or equal to about 250° C.

8. The method of claim 1, wherein reacting a silicon chalcogenate precursor and a nitrogen-containing precursor to form silicon nitride comprises reacting the silicon chalcogenate precursor and the nitrogen-containing precursor in a plasma-free environment.

9. A method of forming silicon nitride, comprising:
reacting a silicon chalcogenate precursor with a substrate to form silicon on the substrate, the silicon chalcogenate precursor comprising the chemical formula of $Si(XR^1)_n R^2_{4-n}$, where X is sulfur, selenium, or tellurium, $R^1$ is hydrogen, an alkyl group, a substituted alkyl group, an alkoxide group, a substituted alkoxide group, an amide group, a substituted amide group, an amine group, a substituted amine group, or a halogen group, each $R^2$ is independently hydrogen, an alkyl group, a substituted alkyl group, an alkoxide group, a substituted alkoxide group, an amide group, a substituted amide group, an amine group, a substituted amine group, or a halogen group, and n is 1, 2, 3, or 4;
reacting the silicon with a nitrogen-containing precursor to form nitrogen on the silicon; and
repeating the reacting a silicon chalcogenate precursor and reacting the silicon with a nitrogen-containing precursor acts to form silicon nitride on the substrate.

10. The method of claim 9, wherein reacting a silicon chalcogenate precursor with a substrate to form silicon on the substrate comprises reacting a silicon chalcogenate precursor comprising $Si(XR^1)(R^2)(R^3)(R^4)$, $Si(XR^1)(XR^2)(R^3)(R^4)$, $Si(XR^1)(R^2)(XR^3)(R^4)$, $Si(XR^1)(XR^2)(R^3)(XR^4)$, $Si(XR^1)(XR^2)(XR^3)(R^4)$, $Si(XR^1)(R^2)(XR^3)(XR^4)$, or $Si(XR^1)(XR^2)(XR^3)(XR^4)$ with the substrate.

11. The method of claim 9, wherein reacting a silicon chalcogenate precursor with a substrate to form silicon on the substrate comprises reacting silicon tetramethylselenoate with the substrate.

12. The method of claim 9, wherein reacting the silicon with a nitrogen-containing precursor to form nitrogen on the silicon comprises reacting the silicon with ammonia.

13. A method of forming silicon nitride on a semiconductor structure, comprising:
forming a substrate comprising at least one feature having an aspect ratio of greater than about 10:1; and
reacting a silicon chalcogenate precursor and a nitrogen-containing precursor to form silicon nitride on the at least one feature, the silicon chalcogenate precursor comprising the chemical formula of $Si(XR^1)_n R^2_{4-n}$, where X is sulfur, selenium, or tellurium, $R^1$ is hydrogen, an alkyl group, a substituted alkyl group, an alkoxide group, a substituted alkoxide group, an amide group, a substituted amide group, an amine group, a substituted amine group, or a halogen group, each $R^2$ is independently hydrogen, an alkyl group, a substituted alkyl group, an alkoxide group, a substituted alkoxide group, an amide group, a substituted amide group, an amine group, a substituted amine group, or a halogen group, and n is 1, 2, 3, or 4.

14. The method of claim 13, wherein reacting a silicon chalcogenate precursor and a nitrogen-containing precursor to form silicon nitride on the at least one feature comprises conformally forming the silicon nitride on the at least one feature.

15. The method of claim 13, wherein reacting a silicon chalcogenate precursor and a nitrogen-containing precursor comprises forming the silicon nitride by atomic layer deposition.

16. The method of claim 13, wherein reacting a silicon chalcogenate precursor and a nitrogen-containing precursor comprises forming the silicon nitride by chemical vapor deposition.

17. The method of claim 13, wherein forming a substrate comprising at least one feature having an aspect ratio of greater than about 10 comprises forming the at least one feature on a thermally sensitive substrate.

18. The method of claim 13, wherein reacting a silicon chalcogenate precursor and a nitrogen-containing precursor to form silicon nitride on the at least one feature comprises forming the silicon nitride on the at least one feature etchable by a halide.

* * * * *